US006731965B2

(12) United States Patent
Menon et al.

(10) Patent No.: US 6,731,965 B2
(45) Date of Patent: May 4, 2004

(54) CORROSION PREVENTION IN BIOMEDICAL ELECTRODES

(75) Inventors: Vinod P. Menon, Woodbury, MN (US); Hatim M. Carim, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 326 days.

(21) Appl. No.: 09/885,025

(22) Filed: Jun. 20, 2001

(65) Prior Publication Data

US 2003/0045788 A1 Mar. 6, 2003

(51) Int. Cl.[7] .................................................. A61B 5/04
(52) U.S. Cl. ........................ 600/396; 600/391; 600/392; 600/395; 607/149; 607/152; 607/153
(58) Field of Search ................................. 600/391, 392, 600/395–397; 607/149, 152, 153

(56) References Cited

U.S. PATENT DOCUMENTS

| RE24,906 E | 12/1960 | Ulrich |
| 2,973,826 A | 3/1961 | Barnhart |
| 3,389,827 A | 6/1968 | Abere et al. |
| 4,112,213 A | 9/1978 | Waldman |

(List continued on next page.)

FOREIGN PATENT DOCUMENTS

| EP | 0 051 935 | 5/1982 |
| FR | 2729575 | 7/1996 |
| WO | WO 94/26950 | 11/1994 |

OTHER PUBLICATIONS

Ewins, "Thermoplastic Rubbers: A–B–A Block Copolymers", Chapter 13 of Satas, Ed., Handbook of Pressure Sensitive Adhesive Technology, 2nd Edition, Van Nostrand Reinhold, 1989.
Lippert, "Slot Die Coating for Low Viscosity Fluids", Chapter 11 of Satas, Ed., Coatings Technology Handbook, Marcel Dekker, Inc., 1991.
Satas, "Coating Equipment", Chapter 34 of Satas, Ed., Handbook of Pressure Sensitive Adhesive Technology, 2nd Edition, Van Nostrand Reinhold, 1989.

*Primary Examiner*—Lee Gohen
(74) *Attorney, Agent, or Firm*—John A. Burtis; Daniel R. Pastirik

(57) ABSTRACT

A non-polarizable, silver/silver chloride biomedical electrode that is protected against corrosion during its shelf life by an organic corrosion retarding agent, preferably selected from the group consisting of mercaptans and azoles.

22 Claims, 2 Drawing Sheets

U.S. PATENT DOCUMENTS

| | | | |
|---|---|---|---|
| 4,204,312 A | | 5/1980 | Tooker |
| 4,235,241 A | | 11/1980 | Tabuchi et al. |
| 4,310,509 A | | 1/1982 | Berglund et al. |
| 4,323,557 A | | 4/1982 | Rosso et al. |
| 4,352,359 A | | 10/1982 | Larimore et al. |
| 4,370,984 A | | 2/1983 | Cartmell |
| 4,377,170 A | | 3/1983 | Carim |
| 4,391,278 A | * | 7/1983 | Cahalan et al. ............. 600/391 |
| 4,524,087 A | | 6/1985 | Engel |
| 4,539,996 A | | 9/1985 | Engel |
| 4,554,924 A | | 11/1985 | Engel |
| 4,732,808 A | | 3/1988 | Krampe et al. |
| 4,846,185 A | | 7/1989 | Carim |
| 4,848,348 A | | 7/1989 | Craighead |
| 4,848,353 A | | 7/1989 | Engel |
| 4,917,928 A | | 4/1990 | Heinecke |
| 4,917,929 A | | 4/1990 | Heinecke |
| RE33,353 E | | 9/1990 | Heinecke |
| 5,012,810 A | | 5/1991 | Strand et al. |
| 5,133,356 A | | 7/1992 | Bryan et al. |
| 5,215,087 A | | 6/1993 | Anderson et al. |
| 5,296,079 A | | 3/1994 | Romo |
| 5,338,490 A | | 8/1994 | Dietz et al. |
| 5,385,679 A | | 1/1995 | Uy et al. |
| 5,702,753 A | | 12/1997 | Yasis et al. |
| 5,746,207 A | | 5/1998 | McLaughlin et al. |
| 5,779,632 A | | 7/1998 | Dietz et al. |
| 5,823,957 A | | 10/1998 | Faupel et al. |
| 5,824,033 A | * | 10/1998 | Ferrari ....................... 607/142 |
| 5,952,398 A | | 9/1999 | Dietz et al. |
| 6,019,877 A | | 2/2000 | Dupelle et al. |
| 6,144,871 A | | 11/2000 | Saito et al. |
| 6,232,366 B1 | * | 5/2001 | Wang et al. ................. 600/391 |

* cited by examiner

CORROSION PREVENTION IN BIOMEDICAL ELECTRODES

TECHNICAL FIELD

This invention relates to the making and using of biomedical electrodes.

BACKGROUND OF THE INVENTION

Modern medicine employs many medical procedures where electrical signals or currents are received from or delivered to a patient's body. The interface between medical equipment used in these procedures and the skin of the patient usually includes a biomedical electrode. Such an electrode typically includes a conductor connected electrically to the equipment and a conductive medium adhered to or otherwise in contact with the patient's skin.

Therapeutic procedures and devices that make use of biomedical electrodes include transcutaneous electronic nerve stimulation (TENS) devices for pain management; neuromuscular stimulation (NMS) techniques for treating conditions such as scoliosis; defibrillation electrodes for dispensing electrical energy to a chest cavity to defibrillate the heart; and dispersive electrodes to receive electrical energy dispensed into an incision made during electrosurgery.

Diagnostic procedures that make use of biomedical electrodes include electrocardiograms (ECGs) for monitoring heart activity and diagnosing heart abnormalities.

Representative examples of biomedical electrodes that have been used for, or described as useful for, diagnostic purposes include U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); and 5,296,079 (Duan et al.), the entire contents of which are hereby incorporated by reference.

For diagnostic applications, non-polarizable electrodes, and in particular silver/silver chloride electrodes, have become the current collectors of choice because of their high electrical stability. In low-cost versions, these electrodes are coated in thin sections from a conductive ink containing silver/silver chloride particles and a polymeric binder onto an insulating backing. While silver/silver chloride electrodes are reasonably resistant to corrosive attack and generally have a long shelf-life, under certain gel conditions such as a low pH in conjunction with a high water content and high chloride concentration, they can undergo accelerated corrosion and exhibit premature electrical failure.

To control corrosion in biomedical electrodes, sacrificial anodes have been interwoven in an electrode assembly and electrically connected to a current collector. While functional, such protection may not be cost-effective due to design constraints and added material costs.

Alternative for silver/silver chloride materials have also been proposed for biomedical electrodes, among them titanium hydride and certain carbon-containing materials. Such arrangements, however, are generally unduly complex, expensive and material-intensive.

There remains a need, therefore, for corrosion-resistant biomedical electrodes that are simply constructed and relatively cost-effective.

SUMMARY OF THE INVENTION

In one aspect, the present invention provides a non-polarizable biomedical electrode that is protected against corrosion by an organic corrosion retarding agent. The biomedical electrode comprises a conductor in contact with a conductive medium, wherein the conductor comprises a conductively active source of at least partially chlorided silver and wherein the electrode includes at least one organic corrosion retarding agent.

In another aspect, the invention provides a biomedical electrode comprising a conductor in contact with a conductive medium, wherein the conductor comprises a substrate having at least partially chlorided silver thereon and wherein the silver has been treated with an organic corrosion retarding agent.

In still another aspect, the invention provides methods of preparing biomedical electrodes, the methods generally comprising the steps of:

preparing a conductor having a conductive layer comprising partially chlorided silver and at least one organic corrosion retarding agent; and applying a layer of conductive medium to the conductive layer.

DETAILED DESCRIPTION OF PREFERRED EMBODIMENTS

In one aspect the invention provides a biomedical electrode having a conductor in contact with a conductive medium. The conductor includes a conductive substrate having partially chlorided silver thereon and is protected from corrosion by the presence of at least one organic corrosion retarding agent. The conductive substrate may comprise a polymeric material in the form of a thin film upon which there is a silver-containing layer, or the conductor may comprise a graphite loaded polymer or other conductive material in the form of a stud upon which is a silver-containing layer. The silver-containing layer can contain a silver-loaded ink, a vapor deposit of silver or some other source of active silver. The silver in such a layer may be partially chlorided, either by having silver chloride intrinsic to the applied layer or by separately partially chloriding a silvered surface.

A conductive medium is most conveniently provided for the electrode by a conductive adhesive, although conductive gels and other electrolytes also are considered useful. Conductive adhesives made from polymerized microemulsions, including those described in U.S. Pat. No. 5,952,398, are also considered useful. The corrosion retarding agent may be incorporated into the electrode construction either by treating the partially chlorided silver layer of the conductor with the corrosion retarding agent or by including the agent in the formulation of a silver-loaded ink. The latter may be accomplished by applying the agent to the coated ink layer after it has been applied. The corrosion retarding agent may also be included directly in the conductive medium.

Useful corrosion retarding agents include any agent that adequately retards corrosion and that is compatible with the conductive materials, i.e., does not degrade the electrical properties of the interface between the conductor and the conductive medium. Preferred corrosion retarding agents will also resist leaching into the conductive medium, which could cause a loss of corrosion protection and raise the possibility of dermal contact, and will exhibit low toxicity towards human skin. Since in manufacturing practice it is convenient to place the silver onto the conductor by means of a silver-loaded ink, the agents will also preferably be highly soluble in known solvent carriers for such inks and will have relatively low vapor pressures to withstand the thermal treatment required to dry ink coatings. The most preferred corrosion retarding agents are selected from the group consisting of mercaptans and azoles. Specific, representative compounds include 2-mercaptobenzoxazole and octadecanethiol.

Figure 1:
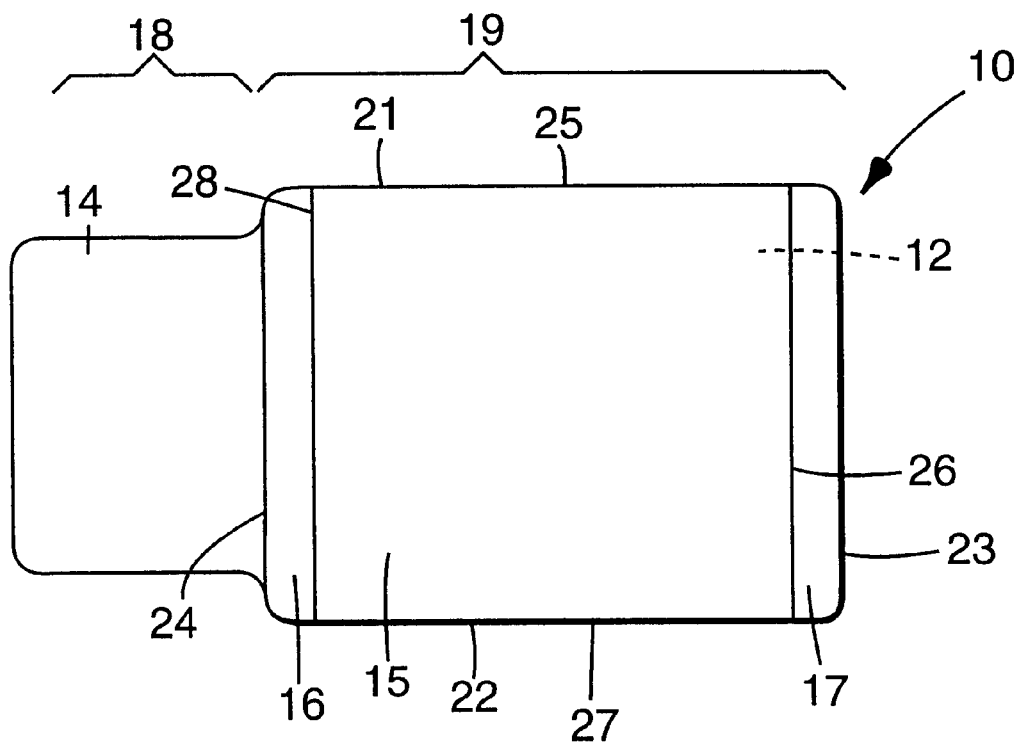
FIG. 1 is a bottom plan view of a diagnostic electrode according to the present invention.
Figure 2:
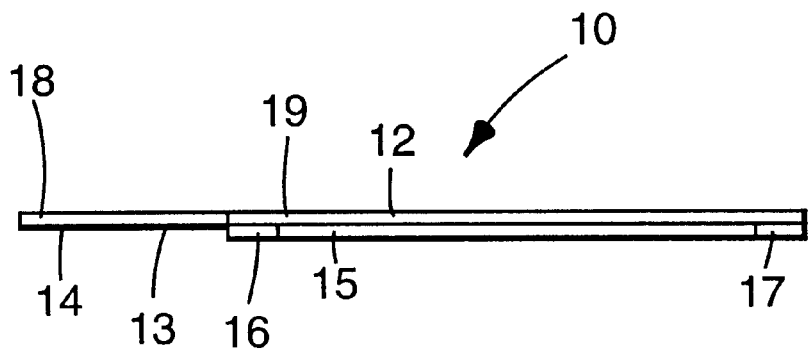
FIG. 2 is a side plan view of the diagnostic electrode of FIG. 1.
Figure 3:
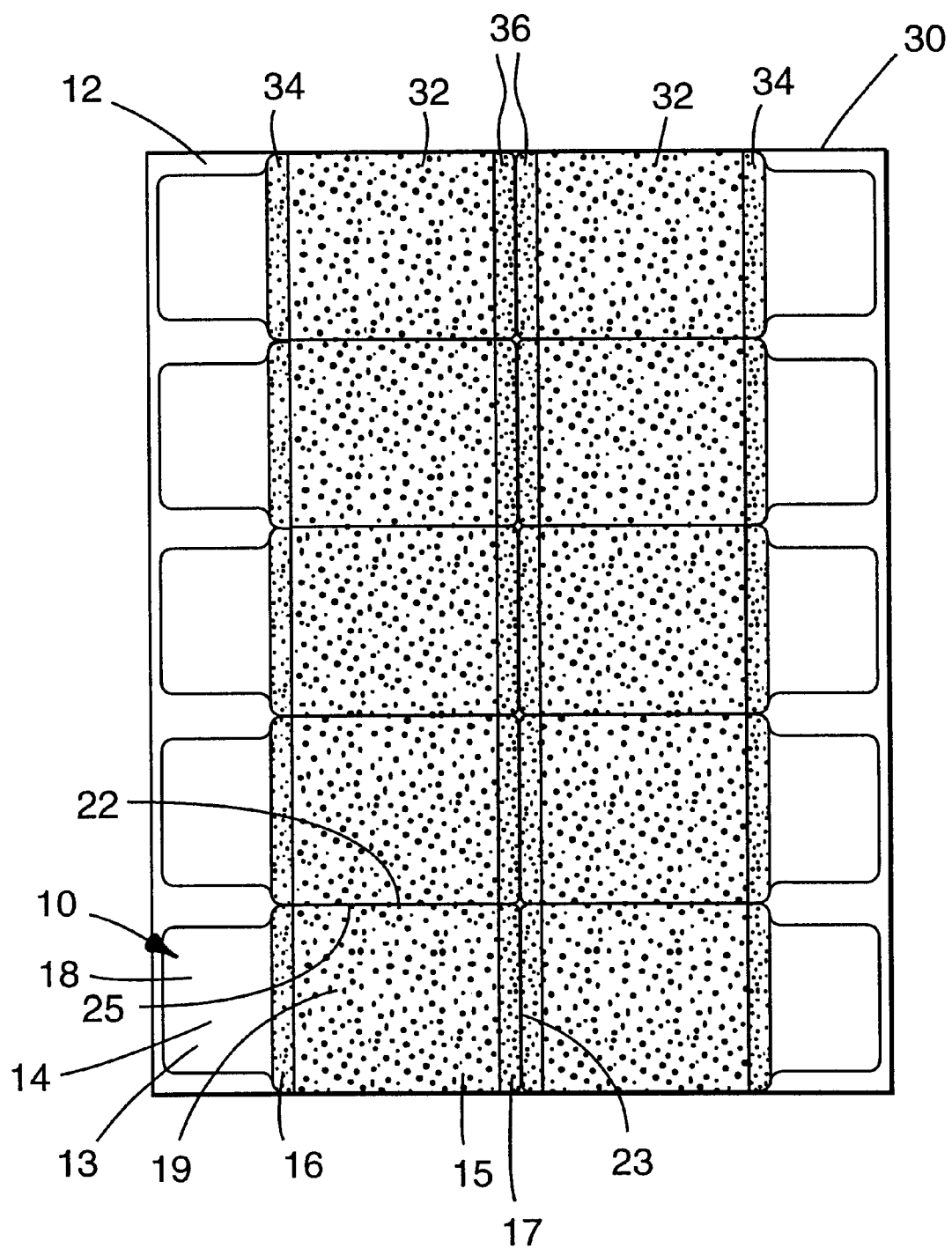
FIG. 3 is an array of diagnostic electrodes during manufacture.

FIGS. 1 and 2 are bottom and side plan views, respectively, of one embodiment of a diagnostic electrode 10 of the present invention. From the surface farthest away from mammalian skin, electrode 10 comprises a nonconductive flexible backing 12 having a side 13 having on at least a portion thereof an electrically conductive surface 14 contacting a field 15 of conductive adhesive. Two separate opposing fields 16 and 17 of biocompatible pressure sensitive skin adhesive contact side 13 and preferably electrically conductive surface 14. Not shown is a release liner that contacts fields 15, 16, and 17 of adhesive when electrode 10 is not in use.

Flexible backing 12 comprises a tab portion 18 and a pad portion 19. Both tab portion 18 and pad portion 19 have electrically conductive surface 14, but field 15 of conductive adhesive contacts only pad portion 19. Tab portion 18 is suitable for releasable attachment to an electrical connector that delivers the ECG signals to the electrical instrumentation.

Pad portion 19 has a perimeter defined by edges 21, 22, 23, and 24. By comparison, field 15 of conductive adhesive has a perimeter defined by edges 25, 26, 27, and 28. The surface area of field 15 of conductive adhesive within edges 25–28 contacts the surface area of pad portion 19 within edges 21–24 of pad portion 19.

Fields 16 and 17 of biocompatible skin adhesive are not ionically conductive as is field 15 but are preferably contacting pad portion 19 in separate locations on side 13 and preferably in separate locations on electrically conductive surface 14 to assist in the maintenance of adhesive contact of electrode 10 to skin of a mammalian patient. The separate opposing locations on pad portion 19 proximal and distal to tab portion 18 provide a relatively high level of adhesion to mammalian skin because the electrode 10 has added adhesiveness in the two locations most likely to be affected by edge lifting of the electrode 10 due to stress applied to the electrode 10 during use: along a line bisecting both the tab portion 18 and the pad portion 19.

As seen in FIG. 2, preferably the biocompatible pressure sensitive skin adhesive fields 16 and 17 is in direct contact with side 13, and preferably electrically conductive surface 14, of pad portion 19. Also preferably, the final thickness (after processing) of fields 16 and 17, ranging from about 0.25 mm to about 0.75 mm thick, and preferably about 0.50 mm thick, is within 40 percent, and preferably within 20 percent, of the final thickness of the field 15 of ionically conductive adhesive. Ideally, the final thickness of field 15 and fields 16 and 17 are equal or within a difference of less than 10 percent.

Selection of materials to construct electrode 10 are known to those skilled in the art of biomedical electrode construction. U.S. Pat. Nos. 4,352,359 (Larimore); 4,524,087 (Engel); 4,539,996 (Engel); 4,554,924 (Engel); 4,848,348 (Carim); 4,848,353 (Engel); 5,012,810 (Strand et al.); 5,133,356 (Bryan et al.); 5,215,087 (Anderson et al.); 5,296,079 (Duan et al.); 5,385,679 (Uy et al.); 5,702,753 (Yasis et al.); and 5,779,632 (Dietz et al) all describe suitable materials for the construction of biomedical electrodes useful for ECG procedures, and all are incorporated by reference as if fully rewritten herein.

Of the numerous electrically nonconductive materials known to those skilled in the art, presently preferred for backing material 12 are polyester films of about 0.1 mm thickness commercially available as "Melinex" branded films (e.g., 329 and 339) from ICI Americas of Hopewell, Va. Preferably, the film can be treated with a corona treatment to improve the adhesion of the electrically conductive surface to the backing material.

Of the numerous electrically conductive materials known to those skilled in the art, inks containing electrical conductive particles such as graphite or metals are useful with metal-containing inks being preferred. Presently preferred for electrically conductive surface 14 is a silver containing ink such as "N-30" ink, a silver/silver chloride containing ink such as "R-300" ink, or R-301 MPK (+240)® ink, all commercially available from Ercon, Inc. of Waltham, Mass. Such a silver/silver chloride ink may be conveniently be applied to a backing by gravure coating. Many other methods are considered suitable, including ink jet printing, silkscreen printing, and knife coating.

Of the numerous conductive adhesives known to those skilled in the art, field 15 of conductive adhesive can be those conductive adhesives as described in the table at column 16 of U.S. Pat. No. 5,012,810 (Strand et al.) and as disclosed in U.S. Pat. Nos. 4,524,087; 4,539,996; 4,848,353; and 4,554,924 (all Engel); U.S. Pat. No. 5,296,079 (Duan et al.); 5,385,679 (Uy et al.); and 5,338,490 (Dietz et al.) all of which are incorporated by reference herein. Presently preferred for field 15 of conductive adhesive is a bicontinuous biocompatible conductive adhesive having interpenetrating domains of hydrophilic and hydrophobic composition as described in U.S. Pat. No. 5,779,632 to Dietz et al, which is incorporated by reference herein. It is sometimes convenient to increase the viscosity of the conductive adhesive of the 5,779,632 reference for ease in coating. Adding a quantity of polyacrylic acid having a molecular weight generally between 200,000 and 800,000 prior to polymerization can be done to accomplish this. Additional details regarding such a process can be found in co-pending U.S. patent application Ser. No. 09/844,031, filed on Apr. 27, 2001 which is incorporated herein by reference.

Of the numerous biocompatible skin adhesives known to those skilled in the art, presently preferred for fields 16 and 17 of adhesive are acrylate pressure sensitive adhesives and tackified polystyrene-polyisoprene block copolymers pressure sensitive adhesives. Such acrylate ester copolymer adhesives are generally described in U.S. Pat. Nos. 2,973,286; Re 24,906; Re 33,353; 3,389,827; 4,112,213; 4,310,509; 4,323,557; 4,732,808; 4,917,928; 4,917,929; and European Patent Publication 0 051 935, all incorporated herein by reference. Tackified block copolymer adhesives are generally described in Ewins, "Thermoplastic Rubbers: A-B-A Block Copolymers" which is Chapter 13 of Satas, Ed., Handbook of Pressure Sensitive Adhesive Technology, Second Edition, Van Nostrand Reinhold, 1989, which is incorporated herein by reference. Use of tackified block copolymer adhesives as biocompatible skin adhesives in biomedical electrodes is described in U.S. Pat. No. 4,204,312.

A variety of coating methods is available for both the conductive adhesive and the biocompatible skin adhesive including extrusion coating, knife coating, and curtain coating as described in Satas, "Coating Equipment" which is Chapter 34 of Satas, Ed., Handbook of Pressure Sensitive Adhesive Technology, Second Edition, Van Nostrand Reinhold, 1989, which is incorporated herein by reference. Hand knife coating can be employed. A slot die is preferably used, which can include an extrusion die, a knife die, a curtain coating die and other types of slot dies with a high shear flat wiping lip, a medium shear flat wiping lip, a medium shear rod wiping lip, or a sharp knife wiping lip, which are generally described in Lippert, "Slot Die Coating for Low Viscosity Fluids", which is Chapter 11 of Satas, Ed., Coatings Technology Handbook, Marcel Dekker, Inc., 1991, which is incorporated by reference herein. The choice of the coating method and use of slot dies depend on the nature of the adhesive precursor, whether it is a high viscosity 100% solids material, a moderate viscosity 100% solids material to be polymerized on-web, or a moderate to low viscosity solvent or water delivered material. One skilled in the art will recognize that in the latter case, the coating step includes a drying process and this drying process results in a final thickness of adhesive that is thinner than the thickness at the coating head due to loss of solvent or water. The final thickness of conductive adhesive should be within 40% of the final thickness of the biocompatible pressure sensitive adhesive in order for both types of adhesive to have contact with the skin of a patient.

ECG Disposable Electrodes" Association for the Advancement of Medical Instrumentation (1984), the disclosure of which is incorporated by reference, for testing methods and conditions for minimum standards for the properties of D.C. Offset (100 mV), A.C. Impedance (2 kOhms), and Defibrillation Overload Recovery (less than 100 mV 5 seconds after 4 capacitor discharges and a rate of change of residual polarization potential no greater than 1 mV/sec.)

These standard AAMI tests were run on some of the electrode pairs immediately after fabrication. Another group of electrodes were aged at 203° F. (95° C.) for 48 hours and also subjected to the AAMI testing. The results are shown in Table 1 below.

TABLE 1

| Composition | Acceptable values → | DC offset (mV) at 60 s (10) | $Z_{10}$ (ohms) (2000) | SDR after 4 pulses (100) | SDR slope (mV/s) (Less than 1) | $Z_{10}$ (ohms) (2000) |
|---|---|---|---|---|---|---|
| Control | unaged | 0.2 | 307 | 11.5 | −0.3 | 171 |
|  | aged | −8.1 | 4022 | 25.9 | −2.3 | 3741 |
| 0.1% MBO | unaged | −0.1 | 147 | 8.7 | −0.3 | 140 |
|  | aged | 0.5 | 4013 | 9.4 | −0.2 | 553 |
| 0.5% MBO | unaged | −3.0 | 416 | 13.4 | −0.4 | 263 |
|  | aged | 0.1 | 257 | 18.0 | −0.7 | 214 |
| 1.0% MBO | unaged | 1.2 | 636 | 18.9 | −0.8 | 475 |
|  | aged | 1.8 | 915 | 33.1 | −2.0 | 851 |

EXAMPLES

Example 1

A silver/silver chloride conductive ink solution commercially available as "R300" was obtained from Ercon Inc. of Waltham, Mass. This ink has a solids content of 58%, of which the elemental silver comprises 70%. The carrier solvent for the ink was methyl propyl ketone (MPK). A quantity of 2-mercaptobenzoxazole (MBO) with a purity of 95% was obtained from Aldrich Chemicals of Milwaukee, Wis. to be the treating agent. Three 100 gram samples of the ink were weighed out. To each of these was added a solution of MBO predissolved in MPK so as to obtain final concentrations of 0.1%, 0.5%, and 1.0% MBO on a weight basis based on elemental silver in the ink. These ink samples were thinly coated onto a polymeric backing made from 0.1 mm polyester mm polyester film commercially available as Melinex™505 from ICI Films, Hopewell, Va., using a wire-coating procedure. The coated film was then dried at room temperature for 5 minutes followed by drying at 200° F. (93° C.) for 5 minutes. A control ink sample (containing no MBO) was coated in exactly the same way.

A bicontinuous adhesive compounded according to the disclosure of U.S. Pat. No. 5,779,632 to Dietz et al, and having a pH of 2.8, was attached to the silver coating for all these samples. The samples were then cut into rectangular electrode pieces that had an exposed tab of silver ink for electrical contact.

Example 2

Immediately after fabrication, electrodes from the control group and from each of the levels of MBO were paired together with other electrodes of similar composition.

These pairs were adhered to each other, their layers of bicontinuous adhesive being placed in contact face-to-face. This arrangement is specified in a standard published by the Association for the Advancement of Medical Instrumentation (AAMI) for determining the proper performance for a biomedical electrode used for ECG Disposable Electrodes, specifically the "American National Standard for Pregelled It can be seen from the control sample in this experiment that aging eventually causes this electrode to develop increased impedance, eventually causing it to become unacceptable for use. Judging by the visual appearance, it is believed that corrosion of the silver/silver chloride interface is the reason for this increase. It is to be noted that a sufficient quantity of MBO appears to protect the electrode from this effect, with the clean visual appearance of the treated samples lending support to this conclusion. However, at a certain point the addition of larger quantities of MBO begins to affect the recovery of the electrode from depolarization, so that a level of about 0.5 percent MBO by weight of elemental silver appears to give optimum results.

Example 3

A larger scale experiment was performed to verify the operability of the invention on a commercial scale and under the conditions of commercial packaging. Polyester film of the type described in Example 1, and bearing indicia on one side, was coated with the silver/silver chloride ink from Example 1 at six levels of concentration of MBO. Once again, the MBO was added to the silver ink as a solution in MEK. The ink was diluted about 5% by the addition of the MBO solution. The MBO content in the 6 coated rolls was 0%, 0.1%, 0.3%, 0.5%, 0.7%, and 0.9% w/w (based on the weight of elemental silver in the coating). These six inks were applied by solvent coater to the polyester film in two passes. It was noted that the first coating pass deposited silver content of approximately 0.7 mg/cm² of the polyester backing, and that the second pass increased the level to approximately 1.5 mg/cm².

All of these coated backings were converted to electrodes generally according to the disclosure of U.S. Pat. No. 5,702,753, creating electrode cards with 10 electrodes per card. The electrode cards were then packed in polyliner pouches, with two cards per pouch. Except for the varying levels of treating agent, the resulting electrodes were similar to the model 2360 resting electrode commercially available from 3M Co. of St. Paul, Minn. Random samples of each level of treating agent were tested immediately according to the AAMI standard, while others were aged and then tested according to the standard. Those pouches were aged at 203° F. (95° C.) for eight days and then allowed to equilibrate to room temperature for one hour before testing. The results are shown in the table below.

TABLE 2

| Composition | Acceptable values → | DC offset (mV) at 60 s (10) | $Z_{10}$ (ohms) (2000) | SDR after 4 pulses (100) | SDR slope (mV/s) (Less than 1) | $Z_{10}$ (ohms) (2000) |
|---|---|---|---|---|---|---|
| Control | unaged | 0.1 | 108 | 11.1 | −0.3 | 71 |
|  | aged | −13.6 | 4005 | 10.7 | −0.7 | 782 |
| 0.1% MBO | unaged | −0.2 | 860 | 11.3 | −0.4 | 330 |
|  | aged | 1.5 | 4036 | 388 | −15.6 | 4055 |
| 0.3% MBO | unaged | −0.1 | 1005 | 11.5 | −0.3 | 442 |
|  | aged | −0.5 | 610 | 18.9 | −1.2 | 535 |
| 0.5% MBO | unaged | −0.4 | 851 | 13.4 | −0.4 | 388 |
|  | aged | −0.6 | 154 | 13.4 | −0.4 | 142 |
| 0.7% MBO | unaged | 0.4 | 953 | 14.3 | −0.4 | 452 |
|  | aged | −0.7 | 238 | 17.0 | −1.0 | 204 |
| 0.9% MBO | unaged | −0.7 | 1205 | 18.6 | −0.6 | 555 |
|  | aged | −1.4 | 4052 | 270 | −13.8 | 4051 |

According to the Van't Hoff rule, 8 days at 95° C. is roughly equivalent to a little over 3 years of aging at room temperature. The results clearly show that MBO addition has a beneficial effect on the corrosion resistance of the electrode and that the optimal MBO inclusion amount for this electrode construction lies between 0.3% and 0.5% based on elemental silver content. However, it is believed that the minimum level of agent that provides a useful level of protection against corrosion is dependent on the absolute value of the amount of silver present per square area. It is further believed that as little as 0.01% of MBO by weight of elemental silver content would provide a workable electrode according to the present invention in some alternate constructions having more silver content.

Example 4

Electrode samples were made generally according to Example 1, except that the treating agent was octadecanethiol (OT), added in the amount of 0.1 percent by weight of the elemental silver content of the ink. The samples were then aged at 150° F. (65° C.) for 49 days. The samples were then tested according to the AAMI standard. The results are described the table below.

TABLE 3

| Composition | Acceptable values → | DC offset (mV) at 60 s (10) | $Z_{10}$ (ohms) (2000) | SDR after 4 pulses (100) | SDR slope (mV/s) (Less than 1) | $Z_{10}$ (ohms) (2000) |
|---|---|---|---|---|---|---|
| Control | aged | −3.1 | 4034 | 9.5 | −0.4 | 4023 |
| 0.1% OT | aged | −1.6 | 387 | 12 | −0.2 | 166 |

The example demonstrates that treating agents that may be used in connection with the present invention may have some hydrophobic character and still be functional. However, the amount of such hydrophobic agents that may be used is limited. It was observed that larger amounts of such agents modified the surface energy of the conductive layer, which affected the wetting of the silver/silver chloride surface by the conductive adhesive.

We claim:

1. A biomedical electrode comprising a conductor in contact with a conductive medium, wherein the conductor comprises a conductively active source of at least partially chlorided silver and wherein the electrode further comprises at least one organic corrosion retarding agent present in an amount of at least 0.01 percent by weight of elemental silver in the conductor.

2. The biomedical electrode of claim 1 wherein the conductor comprises a polymeric material in the form of a film upon one side of which is disposed a layer of partially chlorided silver.

3. The biomedical electrode of claim 1 wherein the conductor comprises a graphite loaded polymer.

4. The biomedical electrode of claim 1 wherein the conductor comprises a graphite loaded polymer in the form of a stud upon the outer surface of which is disposed a layer of partially chlorided silver.

5. The biomedical electrode according to claim 1 wherein the organic corrosion retarding agent is selected from the group consisting of mercaptans and azoles.

6. The biomedical electrode according to claim 1 wherein the agent is present in an amount between about 0.1 percent and 1.0 percent by weight of elemental silver in the conductor.

7. The biomedical electrode according to claim 1 wherein the agent is present in an amount between about 0.3 percent and 0.5 percent by weight of elemental silver in the conductor.

8. The biomedical electrode according to claim 1 wherein the conductor comprises a backing having silver/silver chloride containing ink thereon.

9. A biomedical electrode, comprising a conductor in contact with a conductive medium, wherein the conductor comprises a substrate having at least partially chlorided silver thereon, wherein the silver has been treated with an organic corrosion retarding agent.

10. The biomedical electrode according to claim 9 wherein the organic corrosion retarding agent is selected from the group consisting of mercaptans and azoles.

11. The biomedical electrode according to claim 9 wherein the agent is present in an amount of at least 0.01 percent by weight of elemental silver in the conductor.

12. The biomedical electrode according to claim 9 wherein the agent is present in an amount between about 0.1 percent and 1.0 percent by weight of elemental silver in the conductor.

13. The biomedical electrode according to claim 9 wherein the agent is present in an amount between about 0.3 percent and 0.5 percent by weight of elemental silver in the conductor.

14. The biomedical electrode according to claim 9 wherein the conductor comprises a backing having silver/silver chloride containing ink thereon.

15. The biomedical electrode according to claim 9 wherein the agent is selected the group consisting of 2-mercaptobenzoxazole and octadecanethiol.

16. A method of preparing a biomedical electrode, comprising the steps of:

preparing a conductor having a conductive layer comprising partially chlorided silver and at least one organic corrosion retarding agent; and applying a layer of conductive medium to the conductive layer.

17. The method according to claim 16 wherein the conductor comprises a backing having a silver/silver chloride ink thereon.

18. The method of preparing a biomedical electrode according to claim 16 wherein the agent is selected the group consisting of mercaptans and azoles.

19. The method of preparing a biomedical electrode according to claim 16 wherein the agent is selected from the group consisting of 2-mercaptobenzoxazole and octadecanethiol.

20. The biomedical electrode according to claim 16 wherein the agent is present in an amount of at least 0.01 percent by weight of elemental silver in the conductor.

21. The biomedical electrode according to claim 16 wherein the agent is present in an amount between about 0.1 percent and 1.0 percent by weight of elemental silver in the conductor.

22. The biomedical electrode according to claim 16 wherein the agent is present in an amount between about 0.3 percent and 0.5 percent by weight of elemental silver in the conductor.

* * * * *